US008076424B2

(12) United States Patent
Kramer et al.

(10) Patent No.: US 8,076,424 B2
(45) Date of Patent: *Dec. 13, 2011

(54) HEAT-CURABLE COMPOSITIONS COMPRISING LOW-TEMPERATURE IMPACT STRENGTH MODIFIERS

(75) Inventors: Andreas Kramer, Zürich (CH); Jürgen Finter, Zürich (CH); Ulrich Gerber, Uitikon-Waldegg (CH)

(73) Assignee: Sika Technology AG, Baar (CH)

( * ) Notice: Subject to any disclaimer, the term of this patent is extended or adjusted under 35 U.S.C. 154(b) by 664 days.

This patent is subject to a terminal disclaimer.

(21) Appl. No.: 10/564,889

(22) PCT Filed: Jul. 16, 2004

(86) PCT No.: PCT/EP2004/051519
§ 371 (c)(1),
(2), (4) Date: Feb. 7, 2006

(87) PCT Pub. No.: WO2005/007720
PCT Pub. Date: Jan. 27, 2005

(65) Prior Publication Data
US 2007/0066721 A1    Mar. 22, 2007

(51) Int. Cl.
C08F 283/04    (2006.01)
(52) U.S. Cl. ........ 525/454; 525/458; 525/399; 525/407; 156/330
(58) Field of Classification Search .............. 525/454, 525/458, 399, 407; 156/330
See application file for complete search history.

(56) References Cited

U.S. PATENT DOCUMENTS

| | | | |
|---|---|---|---|
| 3,148,167 A * | 9/1964 | Keplinger, Jr. ................ 523/455 |
| 3,505,283 A | 4/1970 | Dalhuisen | |
| 3,533,983 A | 10/1970 | Hirosawa | |
| 4,383,068 A | 5/1983 | Brandt | |
| 4,486,556 A * | 12/1984 | Kordomenos et al. ........ 523/400 |
| 4,952,645 A | 8/1990 | Mülhaupt et al. | |
| 5,073,601 A | 12/1991 | Mulhaupt et al. | |
| 5,079,094 A | 1/1992 | Kimball | |
| 5,151,327 A | 9/1992 | Nishiyama et al. | |
| 5,189,081 A | 2/1993 | Akutagawa et al. | |
| 5,274,006 A | 12/1993 | Kagoshima et al. | |
| 5,278,257 A | 1/1994 | Mulhaupt et al. | |
| 5,290,857 A | 3/1994 | Ashida et al. | |
| 5,350,825 A | 9/1994 | Konig et al. | |
| 5,484,853 A | 1/1996 | Chen et al. | |
| 5,668,227 A | 9/1997 | Wolleb et al. | |
| 5,686,509 A | 11/1997 | Nakayama et al. | |
| 5,707,439 A | 1/1998 | Takekoshi et al. | |
| 5,908,911 A | 6/1999 | Nakashio et al. | |
| 6,077,884 A | 6/2000 | Hess et al. | |
| 6,153,709 A | 11/2000 | Xiao et al. | |
| 6,197,849 B1 | 3/2001 | Zilg et al. | |
| 6,207,733 B1 | 3/2001 | Feola et al. | |
| 6,248,204 B1 | 6/2001 | Schuft | |
| 6,322,890 B1 | 11/2001 | Barron et al. | |
| 6,548,593 B2 | 4/2003 | Merz et al. | |
| 6,649,706 B1 | 11/2003 | Heid et al. | |
| 6,740,192 B1 * | 5/2004 | Lu et al. ................... 156/330 |
| 6,903,180 B2 * | 6/2005 | Kaji et al. .................. 528/96 |
| 2002/0007003 A1 * | 1/2002 | Merz et al. ................ 524/507 |
| 2002/0061970 A1 * | 5/2002 | Sawada ..................... 525/107 |
| 2003/0105266 A1 | 6/2003 | Suga | |
| 2005/0209401 A1 | 9/2005 | Lutz et al. | |
| 2007/0066721 A1 | 3/2007 | Kramer et al. | |
| 2007/0105983 A1 | 5/2007 | Kramer et al. | |
| 2008/0073029 A1 | 3/2008 | Kramer | |
| 2009/0264558 A1 | 10/2009 | Kramer et al. | |
| 2009/0288766 A1 | 11/2009 | Kramer et al. | |
| 2009/0324958 A1 | 12/2009 | Schulenburg et al. | |

FOREIGN PATENT DOCUMENTS

| | | |
|---|---|---|
| DE | 197 51 143 A | 5/1998 |
| DE | 199 24 170 A1 | 11/2000 |
| EP | 0 338 985 B1 | 10/1989 |
| EP | 0 338 995 | 10/1989 |
| EP | 0 343 676 A2 | 11/1989 |
| EP | 0 343 676 B1 | 11/1989 |
| EP | 0 343 686 A1 | 11/1989 |
| EP | 0 353 190 | 1/1990 |
| EP | 0 600 314 A1 | 6/1994 |
| EP | 1 152 019 | 11/2001 |
| EP | 1 359 202 | 11/2003 |

(Continued)

OTHER PUBLICATIONS

Non-Final Rejection in U.S. Appl. No. 12/311,046 mailed Nov. 2, 2009.
International Search Report for International Application No. PCT/EP2007/056598 mailed Aug. 29, 2007.
International Search Report for International Application No. PCT/EP2006/063891 mailed Sep. 25, 2006.
Derwent accession No. 2001-062546 for German Patent No. 19,924,170 and U.S. Patent No. 6,649,706, Heid et al., Nov. 30, 2000, one page.
Derwent accession No. 2002-124066 for European Patent No. 1/152,019 and U.S. Patent No. 6,548,593, Merz et al., Nov. 7, 2001, one page.

(Continued)

Primary Examiner — Randy Gulakowski
Assistant Examiner — Alicia Toscano
(74) Attorney, Agent, or Firm — Oliff & Berridge, PLC

(57) ABSTRACT

The present invention relates to compositions which contain at least one epoxide adduct A having on average more than one epoxide group per molecule, at least one polymer B of the formula (I), at least one thixotropic agent C, based on a urea derivative in a nondiffusing carrier material, and at least one curing agent D for epoxy resins, which is activated by elevated temperature. This composition serves in particular as an adhesive and has an extremely high dynamic resistance to cleavage, in particular at low temperatures.
The invention furthermore relates to impact strength modifiers terminated with epoxide groups and of the formula (I). It has been found that these novel impact strength modifiers result in a significant increase in impact strength in epoxy resin compositions, in particular in two-component epoxy resin compositions.

26 Claims, No Drawings

FOREIGN PATENT DOCUMENTS

| | | |
|---|---|---|
| EP | 1 431 325 | 6/2004 |
| EP | 1 498 441 | 1/2005 |
| GB | 1 326 669 | 8/1973 |
| GB | 2 314 085 A | 12/1997 |
| JP | 2000-212504 A | 8/2000 |
| WO | WO 00/37520 A1 | 6/2000 |
| WO | WO 00/37554 A1 | 6/2000 |
| WO | WO 01/23466 A1 | 4/2001 |
| WO | WO/02/48235 * | 6/2002 |
| WO | WO 03/093387 A1 | 11/2003 |
| WO | WO 2004/055092 A1 | 7/2004 |
| WO | WO 2005/007720 A1 | 1/2005 |
| WO | WO 2005/007766 | 1/2005 |
| WO | WO 2005/007766 A1 | 1/2005 |

OTHER PUBLICATIONS

Non-Final Rejection in U.S. Appl. No. 11/976,991 mailed Nov. 3, 2009.

International Search Report for International Application No. PCT/EP/03/14382 mailed Apr. 7, 2004.

Non-Final Rejection mailed Nov. 18, 2009 in U.S. Appl. No. 10/538,877.

International Search Report for International Application No. PCT/EP2007/061416, filed Feb. 6, 2008.

Office Action in U.S. Appl. No. 11/988,290 mailed Dec. 28, 2010.

Notice of Allowance in U.S. Appl. No. 11/988,290, mailed Jun. 28, 2011.

* cited by examiner

HEAT-CURABLE COMPOSITIONS COMPRISING LOW-TEMPERATURE IMPACT STRENGTH MODIFIERS

FIELD OF THE INVENTION

The invention relates to heat-curable compositions which simultaneously have high impact strength and good mechanical properties at low temperatures down to −40° C. and in particular can be used as one-component adhesives, and impact strength modifiers for epoxy resins at low temperatures.

DESCRIPTION OF THE PRIOR ART

In the manufacture of both vehicles and add-on parts or machines and devices, high-quality adhesives are more and more frequently being used instead of or in combination with conventional joining methods, such as screwing, riveting, punching or welding. This gives rise to advantages and new possibilities in manufacture, for example the manufacture of composite and hybrid materials, or greater freedom in the design of components. For an application in vehicle manufacture, the adhesives must have good adhesion to all substrates used, in particular electrolytically galvanized, hot-galvanized and subsequently phosphated steel sheets, oiled steel sheets and various, optionally surface-treated, aluminum alloys. These good adhesion properties must be maintained in particular even after aging (alternating climatic conditions, salt spray baths, etc.) without major deterioration in quality. If the adhesives are used as body-shell construction adhesives in automotive construction, the stability of these adhesives to cleaning baths and dip coating (so-called wash-out stability) is of major importance in order to be able to guarantee the manufacturer's process reliability.

The adhesives for body-shell construction must cure under the conventional baking conditions of, ideally, 30 min at 180° C. Furthermore, however, they must also be stable up to about 220° C. Further requirements for such a cured adhesive or the adhesive bond include the assurance of operational reliability both at high temperatures up to about 90° C. and at low temperatures down to about −40° C. Since these adhesives are structural adhesives and these adhesives therefore adhesively bond structural parts, high strength and impact strength of the adhesive are of the greatest importance.

It is true that conventional epoxy adhesives are distinguished by high mechanical strength, in particular high tensile strength. However, when the adhesive bond is subjected to impact, classical epoxy adhesives are generally too brittle and are therefore far from able to satisfy the requirements, in particular of the automotive industry, under crash conditions under which both great tensile stresses and cleavage stresses occur. In this respect, in particular the strengths at high temperatures, but in particular at low temperatures (<−10° C.), are often insufficient.

The literature proposes substantially two methods for being able to reduce the brittleness of epoxy adhesives and hence being able to increase the impact strength: firstly, the aim can be achieved by the admixing of at least partly crosslinked high molecular weight compounds, such as latices of core-shell polymers or other flexibilizing polymers and copolymers. Secondly, a certain increase in strength can also be achieved by introducing flexible segments, for example by the corresponding modification of the epoxide components.

According to the first-mentioned technique corresponding to the teaching in the U.S. Pat. No. 5,290,857, epoxy resins can be made more impact-resistant by mixing a fine, pulverulent core-shell polymer into the epoxide matrix. As a result, highly resilient domains which increase the impact strength form in the rigid brittle epoxide matrix. Such core-shell polymers are described in U.S. Pat. No. 5,290,857 and are based on acrylate or methacrylate polymers.

According to the second-mentioned technique, epoxy resin compositions are described in U.S. Pat. No. 4,952,645, which compositions have been flexibilized by the reaction with aliphatic, cycloaliphatic or aromatic carboxylic acids, in particular di- or trimeric fatty acids, and with carboxylic acid-terminated aliphatic or cycloaliphatic diols. Such compositions are said to be distinguished by an increased flexibility in particular at low temperatures.

EP 0 343 676 describes a reactive hotmelt epoxy adhesive comprising a polyurethane-epoxide adduct. The terminal isocyanate groups of prepolymers are reacted with at least one epoxy resin containing hydroxyl groups and having an OH functionality greater than 2, so that a hotmelt adhesive which is solid at room temperature is obtained.

It is also known that epoxy resins can be flexibilized with reactive elastomers, such as, for example, synthetic rubbers and derivatives thereof. The main effect in relation to the imparting of tough and resilient properties is based on the only partial miscibility of the epoxy resins and the corresponding derivatized synthetic rubbers, with the result that heterodisperse phases which have an effect comparable to the core-shell polymer form in the production process. However, the establishment of this superstructure is very dependent both on the quantitative composition and on the procedure during the curing process. The result of this is that a continuous constant quality is very difficult to achieve.

Elastomers which have terminal phenol groups and are prepared by reacting isocyanate-terminated prepolymers with a large excess of bisphenols are described in EP 0307666 A1 as being particularly advantageous for the impact strength modification of epoxy resins. The high phenol content, which has an adverse effect on the storage stability of the formulated system and can lead to expulsion of gases during the curing at 180° C., is disadvantageous for the formulation with epoxides.

In general, latent curing agents, such as dicyandiamide, are used for the high-temperature curing of the epoxy resins described above. High-temperature curing by means of phenol curing agents, such as bisphenols or novolaks, is also known. They lead to advantageously cured adhesives having high glass transition temperatures but are under discussion because of ecological aspects.

SUMMARY OF THE INVENTION

It is the object of the present invention to provide novel impact strength modifiers for epoxy resin compositions, which modifiers contain in particular no free phenol and are suitable for use at low temperatures, in particular temperatures lower than −20° C. These impact strength modifiers should preferably be suitable as a component of one-component and heat-curable compositions stable at room temperature, in particular adhesives and hotmelt adhesives.

Surprisingly, it has been found that this can be achieved by the use of polymeric compounds terminated with epoxide groups and of the general formula (I):

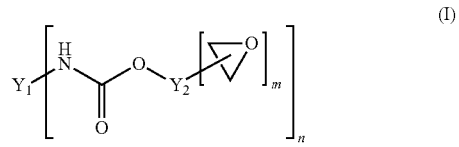

in which $Y_1$ is an n-valent radical of a linear or branched polyurethane prepolymer terminated with isocyanate groups after removal of the terminal isocyanate groups and $Y_2$ is a radical of an aliphatic, cycloaliphatic, aromatic or araliphatic epoxide containing a primary or secondary hydroxyl group after removal of the hydroxide and epoxide groups, and n is 2, 3 or 4, and m is 1, 2 or 3. The polymer of the formula (I) additionally has at least one aromatic structural element which is bound in the polymer chain via urethane groups.

It has been found that this polymer of the formula (I) is a good impact strength modifier.

A particular aspect of the invention is a composition which comprises at least one epoxide adduct A having on average more than one epoxide group per molecule and at least one polymer B of the formula (I) and at least one thixotropic agent C based on a urea derivative in a nondiffusing carrier material and at least one curing agent D for epoxy resins which is activated by elevated temperature.

This composition serves in particular as an adhesive and has an extremely high dynamic resistance to cleavage, in particular at low temperatures.

According to preferred embodiments, compositions which additionally comprise at least one filler E and/or at least one reactive diluent F are furthermore described.

The invention furthermore relates to impact strength modifiers of the formula (I) which are terminated with epoxide groups. It has been found that these novel impact strength modifiers result in a significant increase in impact strength in epoxy resin compositions, in particular 1-component heat-curable epoxy resin compositions and in 2-component epoxy resin compositions.

DESCRIPTION OF THE PREFERRED EMBODIMENTS

The present invention relates to compositions which comprise at least one epoxide adduct A having on average more than one epoxide group per molecule, at least one polymer B of the formula (I), at least one thixotropic agent C based on a urea derivative in a non-diffusing carrier material and at least one curing agent D for epoxy resins which is activated by elevated temperature.

The epoxide adduct A is an epoxide adduct A1 or an epoxide adduct A2.

The epoxide adduct A1 is obtainable from the reaction of at least one dicarboxylic acid and at least one diglycidyl ether. The epoxide adduct A2 is obtainable from the reaction of at least one bis(aminophenyl) sulfone isomer or of at least one aromatic alcohol and at least one diglycidyl ether.

The dicarboxylic acid used for the preparation of the epoxide adduct A1 is preferably a dimeric fatty acid. Dimeric $C_4$-$C_{20}$ fatty acids which are $C_8$-$C_{40}$ dicarboxylic acids have been found to be particularly suitable.

The diglycidyl ethers are preferably a liquid resin, in particular diglycidyl ether of bisphenol A (DGEBA), of bisphenol F and of bisphenol A/F (the designation "A/F" refers here to a mixture of acetone with formaldehyde, which is used as a starting material in the preparation thereof). Owing to the processes for the preparation of these resins, it is clear that the liquid resins also contain higher molecular weight components. Such liquid resins are obtainable, for example, as Araldite GY 250, Araldite PY 304, Araldit GY 282 (Vantico) or D.E.R 331 (Dow).

The epoxide adduct A1 has a flexibilizing character.

The epoxide adduct A2 is obtainable by the reaction of at least one bis(aminophenyl) sulfone isomer or at least one aromatic alcohol with at least one diglycidyl ether. The aromatic alcohol is preferably selected from the group consisting of 2,2-bis(4-hydroxyphenyl)propane (=bisphenol A), bis(4-hydrocyphenyl)methane (=bisphenol F), bis(4-hydroxyphenyl) sulfone (bisphenol S), hydroquinone, resorcinol, pyrocatechol, naphthoquinone, naphthoresorcinol, dihydroxynaphthalene, dihydroxyanthraquinone, dihydroxybiphenyl, 3,3-bis(p-hydroxyphenyl)phthalides, 5,5-bis (4-hydroxyphenyl)hexahydro-4,7-methanoindane, 4,4'-[bis (hydroxyphenyl)-1,3-phenylenebis(1-methylethylidene)] (=bisphenol M), 4,4'-[bis(hydroxyphenyl)-1,4-phenylenebis (1-methylethylidene)] (=bisphenol P) and all isomers of the abovementioned compounds. Bis(4-hydroxyphenyl) sulfone is suitable as a particularly preferred aromatic alcohol.

The preferred bis(aminophenyl) sulfone isomers are bis (4,-aminophenyl) sulfone and bis(3-aminophenyl) sulfone.

The preferred diglycidyl ethers are the diglycidyl ethers already described for epoxide adduct A1.

The epoxide adduct A2 tends to have a rigid structure.

The simultaneous presence of epoxide adduct A1 and epoxide adduct A2 in compositions as claimed in claim 1 is particularly preferred.

The epoxide adduct A preferably has a molecular weight of 700-6000 Dalton, preferably 900-4000 Dalton, in particular 1000-3300 Dalton. "Molecular weight" or "molar weight" is understood here and below as meaning the average molecular weight $M_n$.

The epoxide adduct A is prepared in a manner known to the person skilled in the art. Advantageously, an additional amount of the diglycidyl ether or ethers used for the adduct formation is added at the end of the adduct formation and is used as epoxide adduct A premix. In this epoxide adduct A premix, the total proportion of the unreacted diglycidyl ether or ethers is 12-50% by weight, preferably 17-45% by weight, based on the total weight of the epoxide adduct A premix.

"Total proportion" is understood here and below as meaning in each case the sum of all components belonging to this category. If, for example, two different diglycidyl ethers occur simultaneously in the adduct formation, the total proportion of the diglycidyl ethers is to be understood as meaning the sum of these two diglycidyl ethers.

Furthermore, the proportion by weight of the epoxide adduct A premix is advantageously 20-70% by weight, preferably 35-65% by weight, based on the weight of the total composition.

The polymer B can be represented by formula (I)

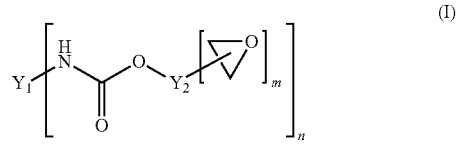

In formula (I), $Y_1$ is an n-valent radical of a linear or branched polyurethane prepolymer terminated with isocyanate groups after removal of the terminal isocyanate groups, and $Y_2$ is a radical of an aliphatic, cycloaliphatic, aromatic or araliphatic epoxide containing a primary or secondary hydroxyl group after removal of the hydroxide and epoxide groups. Furthermore, the indices n are 2, 3 or 4 and the indices m are 1, 2 or 3. In addition, the polymer B has at least one aromatic structural element which is bound in the polymer chain via urethane groups.

The polymer B of the formula (I) is obtainable, for example, by the reaction of a monohydroxy-epoxide compound of the formula (II) and of a linear or branched poly urethane prepolymer terminated with isocyanates groups and of the formula (III):

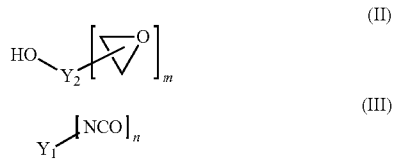

(II)

(III)

For the preparation of the polyurethane prepolymer of the formula (III), at least one polyisocyanate, at least one polyphenol and at least one isocyanate-reactive polymer are used.

In the entire present document, the prefix "poly" in "polyisocyanate", "polyol", "polyphenol" and "polymercaptan" designates molecules which formally contain two or more of the respective functional groups.

Diisocyanates, triisocyanates or tetraisocyanates, in particular di- or triisocyanates, are suitable as the polyisocyanate. Diisocyanates are preferred.

Suitable diisocyanates are aliphatic, cycloaliphatic, aromatic or araliphatic diisocyanates, in particular commercially available products, such as methylenediphenyl diisocyanate (MDI), hexamethylene diisocyanate (HDI), toluene diisocyanate (TDI), tolidine diisocyanate (TODI), isophorone diisocyanate (IPDI), trimethylhexamethylene diisocyanate (TMDI), 2,5- or 2,6-bis(isocyanatomethyl)bicyclo[2.2.1] heptane, 1,5-naphthalene diisocyanate (NDI), dicyclohexylmethyl diisocyanate ($H_{12}$MDI), p-phenylene diisocyanate (PPDI), m-tetramethylxylylene diisocyanate (TMXDI), etc. and the dimers thereof. HDI, IPDI, TMDI, MDI or TDI are preferred.

Suitable triisocyanates are in particular trimers or biurets of aliphatic, cycloaliphatic, aromatic or araliphatic diisocyanates, in particular the isocyanurates and biurets of the diisocyanates described in the preceding paragraph.

Particularly suitable polyphenols are bis-, tris- and tetraphenols. These are understood as meaning not only pure phenols but optionally also substituted phenols. The type of substitution may be very varied. In particular, this is understood as meaning substitution directly on the aromatic nucleus to which the phenolic OH group is attached. Phenols are furthermore understood as meaning not only mononuclear aromatics but also polynuclear or fused aromatics or heteroaromatics which have the phenolic OH group directly on the aromatic or heteroaromatic.

Inter alia, the reaction with isocyanates which is required for the formation of polyurethane prepolymers of the formula (III) is influenced by the type and position of such a substituent.

The bis- and triphenols are particularly suitable. Suitable bisphenols or trisphenols are, for example, 1,4-dihydroxybenzene, 1,3-dihydroxybenzene, 1,2-dihydroxybenzene, 1,3-dihydroxytoluene, 3,5-dihydroxybenzoates, 2,2-bis(4-hydroxyphenyl)propane (=bisphenol A), bis(4-hydroxyphenyl) methane (=bisphenol F), bis(4-hydroxyphenyl)sulfone (=bisphenol S), naphthoresorcinol, dihydroxynaphthalene, dihydroxy-anthraquinone, dihydroxybiphenyl, 3,3-bis(p-hydroxyphenyl)phthalides, 5,5-bis(4-hydroxyphenyl)hexahydro-4,7-methanoindane, phenolphthalein, fluorescein, 4,4'-[bis(hydroxyphenyl)-1,3-phenylenebis(1-methylethylidene)]=bisphenol M), 4,4'-[bis-(hydroxyphenyl)-1,4-phenylenebis(1-methylethylidene)] (=bisphenol P), o,o-diallylbisphenol A, diphenols and dicresols prepared by reacting phenols or cresols with diisopropylidenebenzene, phloroglucinol, gallic ester, phenol novolaks or cresol novolaks having an —OH functionality of from 2.0 to 3.5 and all isomers of the abovementioned compounds.

Preferred diphenols and dicresols prepared by reacting phenols or cresols with diisopropylidenebenzene have a chemical structural formula as shown below for cresols as an example:

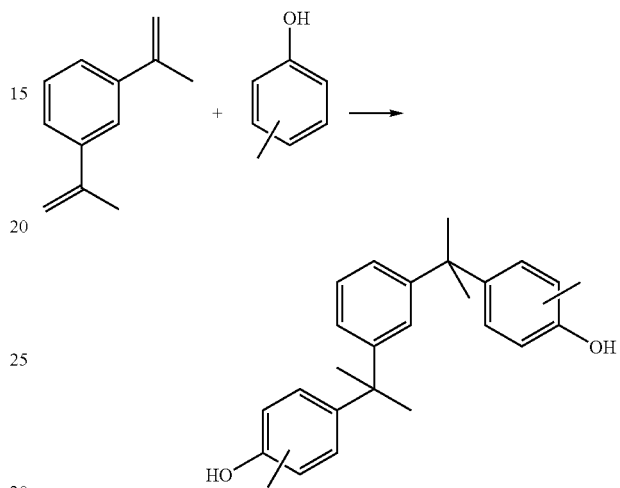

Sparingly volatile bisphenols are particularly preferred. Bisphenol M and bisphenol S are most preferred.

Furthermore, at least one isocyanate-reacting prepolymer is used for the preparation of the polyurethane prepolymer of the formula (III). This isocyanate-reactive polymer has isocyanate-reactive groups which are preferably amino, thiol or hydroxyl groups. These isocyanate-reactive polymers advantageously have an equivalent weight of 600-6000, in particular of 600-4000, preferably of 700-2200, g/equivalent of NCO-reactive groups.

In particular, these isocyanate-reactive polymers are polyols, for example the following commercially available polyols or any desired mixtures thereof:

Polyoxyalkylene polyols, also referred to as polyetherpolyols, which are the polymerization product of ethylene oxide, 1,2-propylene oxide, 1,2- or 2,3-butylene oxide, tetrahydrofuran or mixtures thereof, optionally polymerized with the aid of an initiator molecule having two or three active H atoms, such as, for example, water or compounds having two or three OH groups. It is possible to use both polyoxyalkylenepolyols which have a low degree of unsaturation (measured according to ASTM D-2849-69 and stated in milliequivalents of unsaturation per gram of polyol (meq/g)), prepared, for example, with the aid of so-called double metal cyanide complex catalysts (DMC catalysts for short), and polyoxyalkylenepolyols having a higher degree of unsaturation, prepared, for example, with the aid of anionic catalysts, such as NaOH, KOH or alkali metal alcoholates. Especially suitable are polyoxypropylenediols and -triols having a degree of unsaturation of less than 0.02 meq/g and having a molecular weight in the range of 1000-30000 Dalton, polyoxybutylenediols and triols, polyoxypropylenediols and -triols having a molecular weight of 400-8000 Dalton, and so-called "EO-endcapped" (ethylene oxide-endcapped) polyoxypropylenediols or -triols. The latter are special polyoxypropylenepolyoxyethylenepolyols which are obtained, for example, by a method in which pure polyoxypropylenepolyols are alkoxylated with ethylene oxide after the end of the polypropoxylation and thus have primary hydroxyl groups.

Polyhydroxy-terminated polybutadienepolyols, such as, for example, those which are prepared by a polymerization of 1,3-butadiene and allyl alcohol;

styrene-acrylonitrile-grafted polyetherpolyols, as supplied, for example, by Bayer under the name Lupranol;

polyhydroxy-terminated acrylonitrile/polybutadiene copolymers, as can be prepared, for example, from carboxyl-terminated acrylonitrile/polybutadiene copolymers (commercially available under the name Hycar® CTBN from Hanse Chemie AG, Germany) and epoxides or from amino alcohols;

polyesterpolyols prepared, for example, from dihydric to trihydric alcohols, such as, for example, 1,2-ethanediol, diethylene glycol, 1,2-propanediol, dipropylene glycol, 1,4-butanediol, 1,5-pentanediol, 1,6-hexanediol, neopentylglycol, glycerol, 1,1,1-trimethylolpropane or mixtures of the abovementioned alcohols, with organic dicarboxylic acids or anhydrides or esters thereof, such as, for example, succinic acid, glutaric acid, adipic acid, suberic acid, sebacic acid, dodecanedicarboxylic acid, maleic acid, fumaric acid, phthalic acid, isophthalic acid, terephthalic acid and hexahydrophthalic acid or mixtures of the abovementioned acids, and polyesterpolyols obtained from lactones, such as, for example, ε-caprolactone;

polycarbonatepolyols, as are obtainable by reacting, for example, the abovementioned alcohols—used for the synthesis of the polyesterpolyols—the dialkyl carbonates, diaryl carbonates or phosgene.

The isocyanate-reactive polymers are advantageously difunctional or higher-functional polyols having OH equivalent weights of from 600 to 6000 g/OH equivalent, in particular from 600 to 4000 g/OH equivalent, preferably 700-2200 g/OH equivalent. Furthermore advantageous are the polyols selected from the group consisting of polyethylene glycols, polypropylene glycols, polyethylene glycol/polypropylene glycol block copolymers, polybutylene glycols, hydroxyl-terminated polybutadienes, hydroxyl-terminated butadiene-co-acrylonitriles, hydroxyl-terminated synthetic rubbers and mixtures of these stated polyols.

Furthermore, polyethylene ethers, polypropylene ethers, polybutylene ethers, polybutadienes and polybutadiene/acrylonitriles terminated with difunctional or higher-functional amines, as sold, for example, the under the name Hycar® CTBN by Hanse Chemie AG, Germany, and further amine-terminated synthetic rubbers or mixtures of said components can also be used as isocyanate-reactive polymers.

It is furthermore possible that isocyanate-reactive polymers may also be chain-extended, as can be prepared in the manner known to the person skilled in the art from the reaction of polyamines, polyols and polyisocyanates, in particular from diamines, diols and diisocyanates.

Preferred isocyanate-reactive polymers are polyols having molecular weights of from 600 to 6000 Dalton, selected from the group consisting of polyethylene glycols, polypropylene glycols, polyethylene glycol/polypropylene glycol block polymers, polybutylene glycols, hydroxyl-terminated polybutadienes, hydroxyl-terminated polybutadiene/acrylonitrile copolymers and mixtures thereof.

Particularly preferred isocyanate-reactive polymers are α,ω-polyalkylene glycols having $C_2$-$C_6$-alkylene groups or having mixed $C_2$-$C_6$-alkylene groups, which are terminated with amino, thiol or, preferably, hydroxyl groups. Polypropylene glycol or polybutylene glycol are particularly preferred.

Various possibilities are available for the preparation of the polyurethane prepolymer of the formula (III) from at least one polyisocyanate, at least one polyphenol and at least one isocyanate-reactive polymer.

In a first process, referred to as "one-pot process", a mixture of at least one polyphenol and at least one isocyanate-reactive polymer is reacted with at least one polyisocyanate in an excess of isocyanate.

In a second process, referred to as "2-step process I", at least one polyphenol is reacted with at least one polyisocyanate in an excess of isocyanate and then reacted with less than the stoichiometric amount of at least one isocyanate-reactive polymer.

Finally, in the third process, referred to as "2-step process II", with at least one isocyanate-reactive polymer is reacted with a polyisocyanate in an excess of isocyanate and then with less than the stoichiometric amount of at least one polyphenol.

The three processes lead to isocyanate-terminated polyurethane prepolymers of the formula (III) which, with the same composition, may differ in the sequence of their building blocks. All three processes are suitable, but the "2-step process II" is preferred.

If the isocyanate-terminated polymers of the formula (III) which are described are composed of difunctional units, it was found that the equivalence ratio of isocyanate-reactive polymer/polyphenol is preferably greater than 1.50 and the equivalence ratio of polyisocyanate/(polyphenol+isocyanate-reactive polymer) is preferably greater than 1.20.

If the average functionality of the components used is greater than 2, there is a more rapid increase in molecular weight than in the purely difunctional case. For the person skilled in the art, it is clear that the limits of the possible equivalence ratios depend to a great extent on whether either the chosen isocyanate-reactive polymer, the polyphenol, the polyisocyanate or a plurality of said components have a functionality>2. Depending on circumstances, different equivalence ratios can be established, the limits of which is determined by the viscosity of the resulting polymer and which have to be determined experimentally from case to case.

The polyurethane prepolymer of the formula (III) preferably has a resilient character and possesses a glass transition temperature Tg of less than 0° C.

The monohydroxy-epoxide compound of the formula (II) has 1, 2 or 3 epoxide groups. The hydroxyl group of this monohydroxy-epoxide compound (II) may be a primary or secondary hydroxyl group.

Such monohydroxy-epoxide compounds can be produced, for example, by reacting polyols with epichlorohydrin. Depending on the reaction procedure, the corresponding monohydroxy-epoxide compounds also form in different concentrations as byproducts in the reaction of polyfunctional alcohols with epichlorohydrin. They can be isolated by conventional separation operations. As a rule, however, it is sufficient to use the product mixture obtained in the glycidylation reaction of polyols and comprising polyols completely or partly reacted to give the glycidyl ether. Examples of such hydroxyl-containing epoxides are trimethylolpropane diglycidyl ether (contained as a mixture in trimethylolpropane triglycidyl ether), glyceryl diglycidyl ether (contained as a mixture in glyceryl triglycidyl ether), pentaerythrityl triglycidyl ether (contained as a mixture in pentaerythrityl tetraglycidyl ether). Trimethylolpropane diglycidyl ether, which occurs in a relatively high proportion in customarily prepared trimethylolpropane triglycidyl ether, is preferably used.

However, it is also possible to use other similar hydroxyl-containing epoxides, in particular glycidol, 3-glycidyloxybenzyl alcohol or hydroxymethylcyclohexene oxide. The β-hydroxyether of the formula (VI), which is present in an amount of about 15% in commercially available liquid epoxy resins prepared from bisphenol A (R=CH$_3$) and epichlorohydrin, and the corresponding β-hydroxyethers (VI), which are formed in the reaction of bisphenol F (R=H) or of the mixture of bisphenol A and bisphenol F with epichlorohydrin, are furthermore preferred.

lae (IV) and (V) the compound the linkage point to the remainder of the polymer chain. These structural elements are the result of the reactions for the preparation of the polymer B, which have already been described.

The polymer B advantageously has a resilient character and is furthermore advantageously soluble or dispersible in epoxy resins.

The polymer B can, if required, depending on the resulting viscosity, be diluted with further epoxy resins. Diglycidyl ethers of bisphenol A, bisphenol F and bisphenol A/F, and the reactive diluents F described further below and carrying epoxide groups, in particular hexanediol diglycidyl ether,

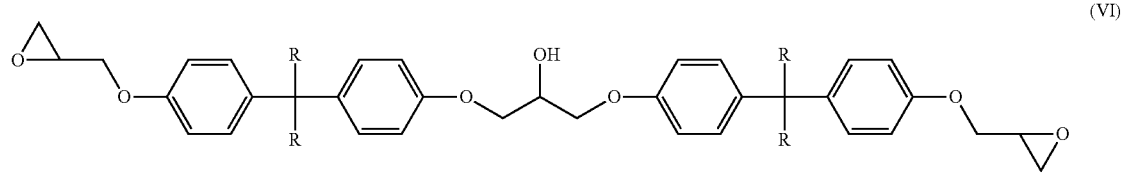

(VI)

Furthermore, it is also possible to use a very wide range of epoxides having a β-hydroxyether group, prepared by the reaction of (poly)epoxides with less than the stoichiometric amount of monovalent nucleophiles, such as carboxylic acids, phenols, thiols or secondary amines.

The free primary or secondary OH functionality of the monohydroxy-epoxide compounds of the formula (II) permits an efficient reaction with terminal isocyanate groups of prepolymers, it also being unnecessary to use disproportionate excess amounts of the epoxide component for this purpose.

The stoichiometric amounts of monohydroxy-epoxide compound of the formula (II) or its mixtures can be used for the reaction of the polyurethane prepolymers of the formula (III). It is possible to depart from the stoichiometry with regard to its equivalents of OH groups and isocyanate groups. The ratio [OH]/[NCO] is from 0.6 to 3.0, preferably from 0.9 to 1.5, in particular from 0.98 to 1.1.

The polymer B has at least one aromatic structural element which is bound in the polymer chain via urethane groups. This structural element can be illustrated by formula (IV). Furthermore, simultaneously present in the polymer chain of the polymer B is a second structural element which can be illustrated by formula (V):

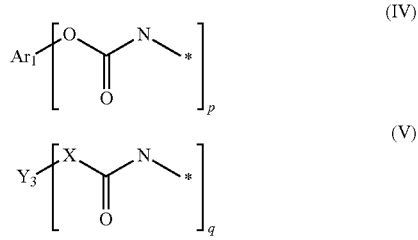

The index p has the values of 2, 3 or 4, in particular p=2 or 3, while the index q has the values of 2, 3 or 4, in particular q=2 or 3. Furthermore, X is S, O or NH, in particular O. The radical Ar$_1$ is a p-valent, optionally substituted, aryl radical. The radical Y$_3$ is a q-valent radical of an optionally chain-extended isocyanate-reactive polymer after removal of the terminal amino, thiol or hydroxyl groups. Finally, * in formupolypropylene glycol diglycidyl ether and trimethylolpropane triglycidyl ether, are preferred for this purpose.

The total proportion of the polymer B is advantageously 5-40% by weight, preferably 7-35% by weight, based on the weight of the total composition.

Furthermore, the composition contains at least one thixotropic agent C, based on a urea derivative in a non-diffusing carrier material. The preparation of such urea derivatives and carrier materials are described in detail in Patent Application EP 1 152 019 A1. The carrier material is advantageously a blocked polyurethane polymer C1, in particular obtained by reacting a trifunctional polyetherpolyol with IPDI and subsequently blocking the terminal isocyanate groups with caprolactam.

The urea derivative is a reaction product of an aromatic monomeric diisocyanate with an aliphatic amine compound. It is also entirely possible to react a plurality of different monomeric diisocyanates with one or more aliphatic amine compounds or a monomeric diisocyanate with a plurality of aliphatic amine compounds. The reaction product of 4,4'-diphenylmethylene diisocyanate (MDI) with butylamine has proven particularly advantageous.

The total proportion of the thixotropic agent C is advantageously 5-40% by weight, preferably 7-25% % by weight, based on the weight of the total composition. The proportion of the urea derivative is advantageously 5-50% by weight, preferably 15-30% by weight, based on the weight of the thixotropic agent C.

The composition according to the invention furthermore contains at least one curing agent D for epoxy resins, which is activated by elevated temperature. It is preferably a curing agent which is selected from the group consisting of dicyandiamide, guanamines, guanidines, aminoguanidines and derivatives thereof. Catalytically active substituted ureas, such as 3-chloro-4-methylphenylurea (chlortoluron), or phenyldimethylureas, in particular p-chlorophenyl-N,N-dimethylurea (monuron), 3-phenyl-1,1-dimethylurea (fenuron) or 3,4-dichlorophenyl-N,N-dimethylurea (diuron) are furthermore possible. Compounds of the class consisting of the imidazoles and amine complexes may furthermore be used. Dicyandiamide is particularly preferred.

The total proportion of the curing agent D is advantageously 1-10% by weight, preferably 2-8% by weight, based on the weight of the total composition.

In a preferred embodiment, the composition contains at least one filler E. This preferably comprises mica, talc, kaolin, wollastonite, feldspar, chlorite, bentonite, montmorillonite, calcium carbonate (precipitated or ground), dolomite, quartz, silicas (pyrogenic or precipitated), cristobalite, calcium oxide, aluminum hydroxide, magnesium oxide, hollow ceramic spheres, hollow glass spheres, hollow organic spheres, glass spheres or colored pigments. Filler E means both the organically coated and the uncoated commercially available forms known to the person skilled in the art.

The total proportion of the total filler E is advantageously 5-30% by weight, preferably 10-25% by weight, based on the weight of the total composition.

In a further preferred embodiment, the composition additionally contains at least one reactive diluent F carrying epoxide groups. These reactive diluents F are in particular:

glycidyl ethers of monofunctional saturated or unsaturated, branched or straight-chain, cyclic or open-chain $C_4$-$C_{30}$ alcohols, e.g. butanol glycidyl ether, hexanol glycidyl ether, 2-ethylhexanol ether, allyl glycidyl ether, tetrahydrofurfuryl and furfuryl glycidyl ether, trimethoxysilyl glycidyl ether, etc.

glycidyl ethers of difunctional saturated or unsaturated, branched or straight-chain, cyclic or open-chain $C_2$-$C_{30}$ alcohols, e.g. ethylene glycol glycidyl ether, butanediol glycidyl ether, hexanediol glycidyl ether, octanediol glycidyl ether, cyclohexanedimethanol diglycidyl ether, neopentylglycol diglycidyl ether, etc.

glycidyl ethers of tri- or polyfunctional, saturated or unsaturated, branched or straight-chain, cyclic or open-chain alcohols, such as epoxidized castor oil, epoxidized trimethylolpropane, epoxidized pentaerythrol or polyglycidyl ethers of aliphatic polyols, such as sorbitol, glycerol, trimethylolpropane, etc.

glycidyl ethers of phenol and aniline compounds, such as phenyl glycidyl ether, cresol glycidyl ether, p-tert-butyl glycidyl ether, nonylphenol diglycidyl ether, 3-n-pentadecenyl glycidyl ether (from cashew nut shell oil), N,N-diglycidylaniline, etc.

epoxidized tertiary amines, such as N,N-diglycidylcyclohexylamine, etc.

epoxidized mono- or dicarboxylic acids, such as glycidyl neodecanoate, glycidyl methacrylate, glycidyl benzoate, diglycidyl phthalate, tetrahydrophthalate and hexahydrophthalate, diglycidyl esters of dimeric fatty acids, etc.

epoxidized di- or trifunctional, low molecular weight to high molecular weight polyetherpolyols, such as polyethylene glycol diglycidyl ether, polypropylene glycol diglycidyl ether, etc.

Hexanediol diglycidyl ether, polypropylene glycol diglycidyl ether and polyethylene glycol diglycidyl ether are particularly preferred.

The total proportion of the reactive diluent F carrying epoxide groups is advantageously 1-7% by weight, preferably 2-6% by weight, based on the weight of the total composition.

It has been found that the composition according to the invention is particularly suitable as one-component adhesives. In particular, it is possible to realize therewith heat-curable one-component adhesives which are distinguished by a high impact strength both at relatively high temperatures and especially at low temperatures, in particular from 0° C. to −40° C. Such adhesives are required for the adhesive bonding of heat-stable materials. Heat-stable materials are understood as meaning materials which are dimensionally stable at a curing temperature of 100-220° C., preferably 120-200° C. at least during the curing time. These are in particular metals and plastics, such as ABS, polyamide, polyphenylene ether, composite materials, such as SMC, unsaturated polyesters glass fiber-reinforced plastics or epoxy or acrylate composite materials. The use in which at least one material is a metal is preferred. The adhesive bonding of identical or different metals, in particular in body-shell construction in the automotive industry, is considered to be a particularly preferred use. The preferred metals are especially steel, in particular electrolytically galvanized, hot-galvanized, oiled steel, bonazinc-coated steel and subsequently phosphated steel, and aluminum, in particular in the variants typically occurring in automotive construction.

In particular, the desired combination of high crash strength and high and low temperature of use can be achieved with an adhesive based on a composition according to the invention.

Such an adhesive is first brought into contact at a temperature of from 10° C. to 80° C., in particular from 10° C. to 60° C., with the materials to be adhesively bonded and is subsequently cured at a temperature of, typically, 100-220° C., preferably 120-200° C.

Of course, in addition to heat-curable adhesives, sealing compounds or coatings can also be realized with a composition according to the invention. Furthermore, the compositions according to the invention are suitable not only for automotive construction but also for other fields of use. Particularly obvious are related applications in construction of means of transport, such as ships, trucks, buses or railway vehicles, or in the construction of consumer goods, such as, for example, washing machines.

The materials adhesively bonded by means of a composition according to the invention are used at temperatures of, typically, from 100° C. to −40° C., preferably from 80° C. to −40° C., in particular from 50° C. to −40° C.

The compositions typically have a fracture energy, measured according to DIN 11343, of more than 10.0 J at −20° C. and more than 7.0 J at −40° C. Fracture energies of more than 11.0 J at −20° C. and of more than 9.0 J at −40° C. are preferred.

Hotmelt adhesives based on the composition according to the invention can also be realized in a special manner. Here, the hydroxyl groups forming in the case of the epoxide adduct A are additionally reacted with polyisocyanate or a polyisocyanate prepolymer. The viscosity is increased thereby, and hot application is required.

A further aspect of the invention relates to novel impact modifiers of the formula (I) of the polymer B which are terminated with epoxide groups and whose detailed constitution and methods of preparation have already been described further above.

It has been found that these impact modifiers of the formula (I) which are terminated with epoxide groups can be added to compositions containing epoxy resins. Systems which can also be formulated without adducts are possible. Both one-component and two-component or multicomponent systems, which may be room temperature-curable or heat-curable, are possible. In addition to the heat-curable, one-component compositions already described, they are also very suitable in the case of two-component or multicomponent epoxy resin compositions, in particular for those whose second component is an amine curing agent or polyamine curing agent or a mercaptan curing agent or a polymercaptan curing agent. The impact modifiers of the formula (I) which are terminated with epoxide groups are added to the curing component, one or more adducts being formed, or, preferably, added to that component which contains the epoxy resin. Further, less preferred, possibilities are the addition of an impact modifier terminated with epoxide groups directly during the application or the addition as a constituent of a third or further component during the application.

The curing temperature of such 2-component or multicomponent epoxy resin compositions is preferably from 10° C. to 60° C., in particular from 15° C. to 50° C. Impact modifiers of the formula (I) which are terminated with epoxide groups are suitable in particular as an additive to 2-component epoxy resin adhesives. Here, the increase in the impact strength is not limited to low temperatures.

Of particular interest is the partial precuring of the impact modifiers according to the invention, which are terminated with epoxide groups, by polyamines or polymercaptans, in particular by diamines and dimercaptans. Thus, the 2-component system can be adjusted so that, as a result of partial precrosslinking, the adhesive acquires a highly viscous to rubber-like consistency which ensures the washout stability in wash processes at temperatures up to 70° C.

These compositions, in particular adhesives, are applied, immediately before the application, by means of a 2-component or multicomponent mixing apparatus to the materials to be brought into contact. Such 2-component or multicomponent adhesives can be used both in automotive construction and in the construction of means of transport (ships, trucks, buses or railway vehicles) or in the construction of consumer goods, such as, for example, washing machines, but also in the building sector, for example as stiffening structural adhesives (inter alia composite materials, etc.).

Such a two-component adhesive can be formulated, for example, in such a way that the impact modifier is a constituent of the first component and at least one polyamine or at least one polymercaptan is a constituent of the second component.

After mixing and curing, such adhesives likewise have good adhesion to the substrates already described above.

EXAMPLES

Some examples which further illustrate the invention but are not intended to limit the scope of the invention in any way are to be described below. The raw materials used in the examples are listed in table 1.

TABLE 1

| Raw materials used. | |
|---|---|
| Raw materials used | Supplier |
| Dimerized C18 fatty acid (Pripol 1013) | Uniqema |
| Triphenylphosphine | Fluka AG |
| Bis(4-hydroxyphenyl)sulfone (=bisphenol S) | Fluka AG |
| Bisphenol A diglycidyl ether (=DGEBA) | Vantico |
| Polypropylene glycol diglycidyl ether (ED-506) | Asah-Denka Kogyo |
| Dicyandiamide (=Dicy) | Degussa |
| Isophorone diisocyanate (=IPDI) | Degussa-Hüls |
| Caprolactam | EMS Chemie |
| N-Butylamine | BASF |
| 4,4'-Diphenylmethylene diisocyanate (=MDI) | Bayer |
| 2,4-Trimethylhexamethylene 1,6-diisocyanate (=TMDI) | Degussa-Hüls |
| Hexanediol diglycidyl ether | Prümmer |
| Desmophen 3060 BS (trifunctional polypropylene glycol, OH equivalent weight = 1000 g/OH equivalent) | Bayer |
| PolyTHF 2000/PolyTHF 2900 (difunctional polybutylene glycol, OH equivalent weight = 1000 and 1450 g/OH eq. respectively) | BASF |

TABLE 1-continued

| Raw materials used. | |
|---|---|
| Raw materials used | Supplier |
| Liquiflex P (hydroxyl-terminated polybutadiene, OH equivalent weight = about 1200 g/OH equivalent) | Petroflex |
| Priplast 2033 (hydroxy-terminated dimerized C18 fatty acid) | Uniqema |
| Bis(hydroxymethyl)tricycle[5.2.1.0(2,6)]decane(=TCD-DM) | Aldrich |
| 4,4'-Isopropylidenedicyclohexanol (=hydrogenated bisphenol A, =A/H) | Aldrich |
| Bisphenol A | Fluka AG |
| 4,4'-[Bis(hydroxyphenyl)-1,3-phenylenebis(1-methylethylidene)] (=bisphenol M) | Mitsui Chemicals |
| Resorcinol | Fluka AG |
| Phenolphthalein | Fluka AG |
| o-Cresol | Fluka AG |
| Lewatit 1131 (anionic ion exchange resin) | BASF |
| 1,3-Diisopropenylbenzene (=m-DIPEP) | Cytec |

General preparation of the epoxide adduct A or of the epoxide adduct A premix:

Example for Epoxide Adduct A Premix: A-VM1

123.9 g of a dimeric fatty acid, 1.1 g of triphenylphosphine and 71.3 g of bis(4-hydroxyphenyl) sulfone were reacted with 658 g of a liquid DGEBA epoxy resin having an epoxide content of 5.45 eq/kg for 5 hours at 110° C. in vacuo and with stirring until a constant epoxide concentration of 2.82 eq/kg was reached. After the end of the reaction, 187.0 g of liquid DGEBA epoxy resin were additionally introduced into the reaction mixture A.

Exemplary Preparation of a Monohydroxyl-Containing Epoxide

Trimethylolpropane glycidyl ether was prepared according to the process in U.S. Pat. No. 5,668,227, example 1, from trimethylolpropane and epichlorohydrin with tetramethylammonium chloride and sodium hydroxide solution. A yellowish product having an epoxide number of 7.5 eq/kg and a hydroxyl group content of 1.8 eq/kg is obtained. From the HPLC-MS spectrum, it is possible to conclude that substantially a mixture of trimethylolpropane diglycidyl ether and trimethylolpropane triglycidyl ether is present.

Exemplary Preparation of a Bisphenol (bis-OK5)

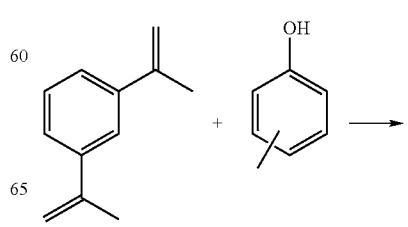

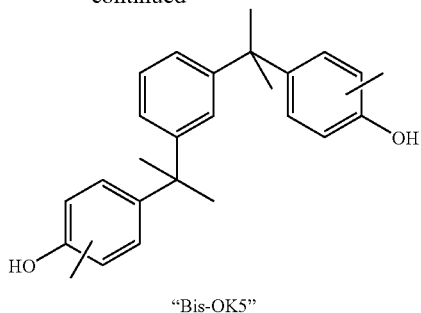

"Bis-OK5"

864 g (8.0 mol) of o-cresol and 100 g of Lewatit-1131 (catalyst) were heated to 67° C. at a pressure of 0.05 bar, and 50 ml of H$_2$O (from Lewatit-1131) were distilled off. 316 g (2.0 mol) of m-DIPEP were then added dropwise under an N$_2$ atmosphere in the course of 1 h, the temperature slowly increasing to 105° C. Stirring was effected for 3 h at 95° C. under the N$_2$ atmosphere. The catalyst was then filtered off through a wire net. At a pressure of 0.05 bar, the temperature was then increased stepwise to 230° C. in the course of 1 h, and it was possible to distill off a total of 500 ml of o-cresol. In this way, 680 g of a highly viscous, honey-yellow material having a residual monomer content of 0.58% and an OH content of about 5 eq/kg were obtained.

Various examples of the preparation of polymer B of the formula (I) are described below.

Example of a Polymer B (According to the Invention): B-01

200 g of PolyTHF 2000 (OH number 57.5 mg/g KOH) were dried for 30 minutes in vacuo at 100° C. 47.5 g of IPDI and 0.04 g of dibutyltin dilaurate were then added. The reaction was carried out in vacuo at 90° C. until the NCO content was constant at 3.6% after 2.5 h (theoretical NCO content: 3.7%). Thereafter, 17.7 g of bisphenol M was added (NCO/OH ratio: 0.45) and stirring was continued in vacuo at 90° C. once again until the NCO content was constant at 2.1% after 3 h (theoretical NCO content: 2.0%). 78.1 g of the trimethylolpropane glycidyl ether described above were then added as monohydroxyl-containing epoxide of the formula (II). Stirring was continued at 90° C. in vacuo until the NCO content had decreased to below 0.1% after a further 3 h. After the end of the reaction, 82.9 g of DGEBA were added (⅓ of the mass of the unblocked, NCO-terminated prepolymer). A clear product having an epoxide content ("end EP content") of 2.51 eq/kg was thus obtained.

Further Polymers B (According to the Invention): B-02 to B-09

Table 2 shows further examples of polymer as are used in compositions according to the invention. These polymers are prepared in the same way as example B-01.

Example of a Polymer P (Not According to the Invention). P-01

200 g of PolyTHF 2000 (OH number 57.5 mg/g KOH) were dried for 30 minutes in vacuo at 100° C. 47.5 g of IPDI and 0.04 g of dibutyltin dilaurate were then added. The reaction was carried out in vacuo at 90° C. until the NCO content was constant at 3.6% after 2.5 h (theoretical NCO content: 3.7%). 123.7 g of the trimethylolpropane glycidyl ether described above were then added as monohydroxyl-containing epoxide of the formula (II). Stirring was continued at 90° C. in vacuo until the NCO content had decreased to below 0.1% after a further 3 h. After the end of the reaction, 82.5 g of DGEBA were added (⅓ of the mass of the unblocked, NCO-terminated prepolymer). A clear product having an epoxide content ("end EP content") of 3.15 eq/kg was thus obtained.

P-01 thus contains no polyphenol structural units in the polymer chain.

Further Examples of Polymers P (Not According to the Invention): P-02 to P-05

The polymers P-02 to P-05 are prepared according to table 2 in the same manner as the polymer P-01 or analogously to B-01. In the case of polymer P-02, the same amount of bisphenol M as in example B-01 was used, but bisphenol M it was dissolved in the hot polymer right at the end of the synthesis. The polymer P-02 accordingly contains free, unbound bisphenol M. The polymer P-03, P-04 and P-05 contain aliphatic diols instead of the bisphenol M of example B-01.

TABLE 2

| | | Polymers | | | | | | |
|---|---|---|---|---|---|---|---|---|
| | | B-01 [g] | B-02 [g] | B-03 [g] | B-04 [g] | B-05 [g] | B-06 [g] | B-07 [g] |
| Polyols | OH number[mg/g KOH] | | | | | | | |
| pTHF2000 | 57.5 | 200.0 | 200.0 | 200.0 | 200.0 | 200.0 | 200.0 | |
| pTHF2900 | 40.6 | | | | | | | 200.0 |
| Liquiflex-P | 45.0 | | | | | | | |
| Polyisocyanates | Equiv. wt. [g/eq] | | | | | | | |
| IPDI | 111.2 | 47.5 | 47.5 | 47.5 | 47.5 | | 47.5 | 33.9 |
| TMDI | 105.0 | | | | | 45.9 | | |
| Polyphenols | Equiv. wt. [g/eq] | | | | | | | |
| Bisphenol M | 173.0 | 17.7 | | | | | | |
| Resorcinol | 55.1 | | 5.4 | | | | | |
| Bisphenol A | 114.2 | | | 11.6 | | | | 7.7 |
| Bisphenol S | 125.1 | | | | 12.9 | | | |
| Phenolphthalein | 159.2 | | | | | 15.9 | | |
| Bis-OK5 | approx. 200 | | | | | | 20.2 | |
| Diols | OH number[mg/g KOH] | | | | | | | |
| Priplast 2033 | 207.0 | | | | | | | |
| TCD-DM | 572.0 | | | | | | | |
| Bisphenol-A/H | 467.2 | | | | | | | |

TABLE 2-continued

| Polymers | | | | | | | | |
|---|---|---|---|---|---|---|---|---|
| Epoxides | OH number[mg/g KOH] | | | | | | | |
| Trimethylolpropane di/triglycidyl ether | 101.0 | 78.1 | 65.7 | 79.5 | 74.9 | 74.9 | 74.4 | 50.3 |
| DGEBA | 13.5 | 82.9 | 82.9 | 82.9 | 82.9 | 82.0 | 82.9 | 78.0 |
| Total | [g] | 426.2 | 401.5 | 421.5 | 418.2 | 418.7 | 425 | 369.9 |
| End-EP content | Epoxide content[eq/kg] | 2.51 | 2.43 | 2.55 | 2.53 | 2.57 | 2.51 | 2.25 |

| | | B-08 [g] | B-09 [g] | P-01 [g] | P-02 [g] | P-03 [g] | P-04 [g] | P-05 [g] |
|---|---|---|---|---|---|---|---|---|
| Polyols | OH number[mg/g KOH] | | | | | | | |
| pTHF2000 | 57.5 | | 160.0 | 200.0 | 200.0 | 200.0 | 200.0 | 200.0 |
| pTHF2900 | 40.6 | 200.0 | | | | | | |
| Liquiflex-P | 45.0 | | 40.0 | | | | | |
| Polyisocyanates | Equiv. wt. [g/eq] | | | | | | | |
| IPDI | 111.2 | 33.9 | 46.8 | 47.5 | 47.5 | 47.5 | | 47.5 |
| TMDI | 105.0 | | | | | | 45.9 | |
| Polyphenols | Equiv. wt. [g/eq] | | | | | | | |
| Bisphenol M | 173.0 | 12.2 | 16.9 | | (17.7*) | | | |
| Resorcinol | 55.1 | | | | | | | |
| Bisphenol A | 114.2 | | | | | | | |
| Bisphenol S | 125.1 | | | | | | | |
| Phenolphthalein | 159.2 | | | | | | | |
| Bis-OK5 | approx. 200 | | | | | | | |
| Diols | OH number[mg/g KOH] | | | | | | | |
| Priplast 2033 | 207.0 | | | | | 24.2 | | |
| TCD-DM | 572.0 | | | | | | 9.9 | |
| Bisphenol-A/H | 467.2 | | | | | | | 12.2 |
| Epoxides | OH number[mg/g KOH] | | | | | | | |
| Trimethylolpropane di/triglycidyl ether | 101.0 | 53.0 | 76.9 | 117.5 | 117.5 | 75.7 | 69.6 | 70.2 |
| DGEBA | 13.5 | 78.0 | 82.5 | 82.9 | 82.9 | 82.9 | 82.0 | 82.9 |
| Total | [g] | 377.1 | 423.1 | 447.9 | 447.9 | 430.3 | 407.4 | 412.8 |
| End-EP content | Epoxide content[eq/kg] | 2.31 | 2.52 | 3.15 | 3.06 | 2.42 | 2.48 | 2.51 |

*Bisphenol M was dissolved only after the epoxy termination of the prepolymer

Thixotropic Agent C

As an example of a thixotropic agent C based on a urea derivative in a nondiffusing carrier material, a thixotropic agent C was prepared according to Patent Application EP 1 152 019 A1 in a blocked polyurethane prepolymer using abovementioned raw materials:

Carrier Material: Blocked Polyurethane Prepolymer C1:

600.0 g of a polyetherpolyol (3000 Dalton; OH number 57 mg/g KOH) were reacted with 140.0 g of IPDI in vacuo and with stirring at 90° C. until the isocyanate content remained constant, the isocyanate-terminated prepolymer being obtained. The free isocyanate groups were then blocked with caprolactam (2% excess).

Urea Derivative (HSD1) in Blocked Polyurethane Prepolymer:

68.7 g of MDI flakes were melted in 181.3 g of the blocked prepolymer described above under nitrogen and with gentle heating. 40.1 g of N-butylamine, dissolved in 219.9 g of the blocked prepolymer described above, were then added dropwise in the course of two hours under nitrogen and with rapid stirring. After the end of the addition of the amine solution, the white paste was stirred for a further 30 minutes. Thus, after cooling, a white, soft paste which had a free isocyanate content of <0.1% (proportion of urea derivative about 20%) was obtained.

Example Compositions

Various adhesive compositions according to tables 3 and 4 were prepared as examples.

For comparison with the example compositions Z-01 to Z-09 according to the invention, Ref-01 the highly structural epoxy adhesive Betamate®-1493 (commercially available from Dow-Automotive, Freienbach, Switzerland), Ref-02 and Ref-03, and X-01 to X-04 were used as examples not according to the invention.

After application to electrolytically galvanized steel (eloZn), the adhesives were cured at 50° C. in the course of 30 minutes in an oven at 180° C. All tests were effected one day after cooling of the adhesive bond to room temperature.

TABLE 3

| Compositions according to the invention. | | | | | | | | | |
|---|---|---|---|---|---|---|---|---|---|
| | Z-01 | Z-02 | Z-03 | Z-04 | Z-05 | Z-06 | Z-07 | Z-08 | Z-09 |
| A-VM1 [g] | 55.6 | 55.6 | 55.6 | 55.6 | 55.6 | 55.6 | 55.6 | 55.6 | 55.6 |
| B-01 [g] | 36.0 | | | | | | | | |
| B-02 [g] | | 36.0 | | | | | | | |

TABLE 3-continued

Compositions according to the invention.

|  | Z-01 | Z-02 | Z-03 | Z-04 | Z-05 | Z-06 | Z-07 | Z-08 | Z-09 |
|---|---|---|---|---|---|---|---|---|---|
| B-03 [g] |  | 36.0 |  |  |  |  |  |  |  |
| B-04 [g] |  |  | 36.0 |  |  |  |  |  |  |
| B-05 [g] |  |  |  | 36.0 |  |  |  |  |  |
| B-06 [g] |  |  |  |  | 36.0 |  |  |  |  |
| B-07 [g] |  |  |  |  |  | 36.0 |  |  |  |
| B-08 [g] |  |  |  |  |  |  | 36.0 |  |  |
| B-09 [g] |  |  |  |  |  |  |  | 36.0 | 36.0 |
| C [g] | 10.0 | 10.0 | 10.0 | 10.0 | 10.0 | 10.0 | 10.0 | 10.0 | 10.0 |
| Dicyandiamide (D) [g] | 4.5 | 4.5 | 4.5 | 4.5 | 4.5 | 4.5 | 4.4 | 4.4 | 4.6 |
| Filler mixture (E) [g] | 22.0 | 22.0 | 22.0 | 22.0 | 22.0 | 22.0 | 22.0 | 22.0 | 22.0 |
| Hexanediol diglycidyl ether (F) [g] | 1.5 | 1.5 | 1.5 | 1.5 | 1.5 | 1.5 | 1.5 | 1.5 | 1.5 |
| ED-506 (F) [g] | 2.4 | 2.4 | 2.4 | 2.4 | 2.4 | 2.4 | 2.4 | 2.4 | 2.4 |
| TSS [MPa] | 19.0 | 19.6 | 20.6 | 21.5 | 18.5 | 20.7 | 19.0 | 19.7 | 22.5 |
| $FE^1$ at 50° C. [J] | 13.7 | 14.7 | 14.2 | 15.6 | 12.9 | 15.2 | 14.2 | 12.1 | 15.3 |
| $FE^1$ at 23° C. [J] | 14.5 | 15.0 | 14.2 | 15.6 | 13.3 | 14.9 | 14.4 | 14.5 | 15.8 |
| $FE^1$ at 0° C. [J] | 13.7 | 14.1 | 12.9 | 15.1 | 14.5 | 14.4 | 15.2 | 13.2 | 13.2 |
| $FE^1$ at −20° C. [J] | 11.9 | 11.6 | 11.1 | 12.9 | 11.5 | 11.7 | 13.3 | 12.7 | 13.2 |
| $FE^1$ at −40° C. [J] | 10.7 | 9.9 | 10.2 | 10.0 | 9.1 | 9.6 | 10.4 | 10.9 | 11.9 |

TABLE 4

Reference examples and counter-examples.

|  | Ref-01 | Ref-02 | Ref-03 | X-01 | X-02 | X-03 | X-04 |
|---|---|---|---|---|---|---|---|
| A-VM1 [g] |  | 55.6 | 55.6 | 55.6 | 55.6 | 55.6 | 55.6 |
| P-01 [g] |  | 18.0 | 36.0 |  |  |  |  |
| P-02 [g] |  |  |  | 36.0 |  |  |  |
| P-03 [g] |  |  |  |  | 36.0 |  |  |
| P-04 [g] |  |  |  |  |  | 36.0 |  |
| P-05 [g] |  |  |  |  |  |  | 36.0 |
| C [g] |  | 21.0 | 10.0 | 10.0 | 10.0 | 10.0 | 10.0 |
| Dicyandiamide (D) [g] |  | 4.0 | 4.6 | 4.6 | 4.6 | 4.5 | 4.5 |
| Filler mixture (E) [g] |  | 22.0 | 22.0 | 22.0 | 22.0 | 22.0 | 22.0 |
| Hexanediol diglycidyl ether (F) [g] |  | 1.5 | 1.5 | 1.5 | 1.5 | 1.5 | 1.5 |
| ED-506 (F) [g] |  | 2.4 | 2.4 | 2.4 | 2.4 | 2.4 | 2.5 |
| TSS [MPa] | 19.9 | 19.8 | 20.3 | 13.2 | 21.0 | 19.6 | 19.9 |
| $FE^1$ at 50° C. [J] | 18.0 | 14.3 | 13.8 | 12.9 | 9.0 | 9.7 | 15.0 |
| $FE^1$ at 23° C. [J] | 17.8 | 14.4 | 13.6 | 13.4 | 12.5 | 10.1 | 13.8 |
| $FE^1$ at 0° C. [J] | 16.2 | 14.0 | 12.5 | 11.6 | 7.2 | 10.4 | 12.0 |
| $FE^1$ at −20° C. [J] | 4.2 | 11.9 | 10.3 | 10.1 | 5.3 | 8.7 | 11.6 |
| $FE^1$ at −40° C. [J] | 0.5 | 6.0 | 5.5 | 2.9 | 0.6 | 2.3 | 0.4 |

Test Methods:
Tensile Shear Strength (TSS) (DIN EN 1465)

The test specimens were produced using electrolytically galvanized steel (eloZn) having the dimensions 100×25×0.8 mm; the adhesion area was 25×10 mm with a layer thickness of 0.3 mm. Curing was effected for 30 min at 180° C. The take-off rate was 10 mm/min.

Dynamic Resistance to Cleavage (ISO 11343)

The test specimens were produced using electrolytically galvanized steel (eloZn) having the dimensions 90×25×0.8 mm; the adhesion area was 25×30 mm with a layer thickness of 0.3 mm. Curing was effected for 30 min at 180° C. The take-off rate was 2 m/s. The area under the measured curve (from 25% to 90%, according to DIN 11343) is stated as the fracture energy (FE) in joules.

Results:

The results of the adhesive formulations in tables 3 and 4 show that the combination of high strength and high impact strength can be achieved both at room temperature and at low temperatures down to −40° C. with the compositions according to the invention (Z-01 to Z-09).

The reference example Ref-01 (Betamate®-1493, Dow Automotive) shows good impact strengths at temperatures above 0° C. but has significantly lower values at low temperatures, i.e. below 0° C., in comparison with the adhesives according to the invention.

The reference example Ref-02 contains, as polymer P-01, a polymer terminated with epoxide groups without phenolic structural elements. This example shows considerably improved impact strength values at temperatures down to −20° C. in comparison with Ref-01, but these values decrease markedly at lower temperatures in comparison with the compositions according to the invention.

The reference example Ref-03 is comparable with Ref-02 but firstly has a higher proportion of the polymer P-01 terminated with epoxide groups and secondly has a lower content of thixotropic agent C. The values obtained are comparable with those which were obtained with the adhesive formulation Ref-02.

The compositions X-01 to X-04 not according to the invention each contain the polymers P02 to P05. X-01 shows an impact strength reduction which is substantial especially at low temperatures. Instead of the phenol structural elements, X-02 to X-04 have structural elements originating from aliphatic diols. X-02 to X-04 likewise all exhibit a considerable reduction in the impact strength, particularly at low temperatures.

The compositions Z-01 to Z-09 according to the invention which are summarized in table 3 all have good fracture energies. While the remaining mechanical values, such as tensile shear strength, are maintained, in particular the values at temperatures from 0° C. to −40° C. are greatly improved in comparison with the reference examples from table 4. The positive effect is substantially independent of the diisocyanates and bisphenols used.

The invention claimed is:
1. A composition comprising:
at least one epoxide adduct A having on average more than one epoxide group per molecule;
at least one polymer B of the formula (I)

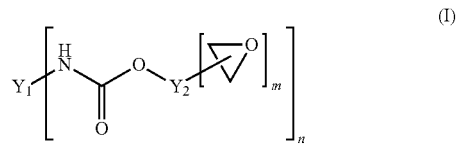

in which:
Y₁ is an n-valent moiety derived from a linear or branched polyurethane prepolymer terminated with isocyanate groups by removal of the terminal isocyanate groups from the polyurethane prepolymer;
Y₂ is a moiety of an aliphatic, cycloaliphatic, aromatic or araliphatic epoxide containing a primary or secondary hydroxyl group after removal of the hydroxide and epoxide groups;
n is 2, 3 or 4;
m is 1, 2 or 3; and
the at least one polymer B has at least one aromatic structural element, which is bound in the polyurethane prepolymer via urethane groups;
wherein the Y₁ moiety of the at least one polymer B simultaneously has at least structural elements of the formulae (IV) and (V)

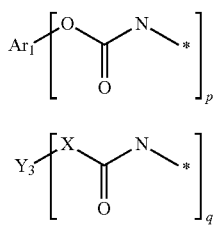

in which:
p is 2, 3 or 4;
q is 2, 3 or 4;
X is S, O or NH;
Ar₁ is a p-valent, optionally substituted, aromatic moiety, wherein the aromatic moiety is directly bound to the urethane groups;
Y₃ is a q-valent moiety of an isocyanate-reactive polymer after removal of the terminal amino, thiol or hydroxyl groups; and
* is the linkage point to the remainder of the polyurethane prepolymer,
wherein the at least one polymer B is obtained from the reaction of a monohydroxyepoxide of the formula (II) and of a linear or branched polyurethane prepolymer terminated with isocyanate groups of the formula (III)

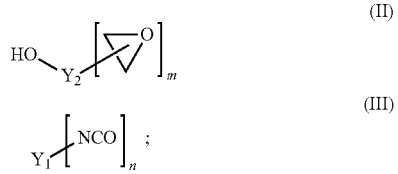

wherein the polyurethane prepolymer of the formula (III) is obtained from the reaction of at least one polyisocyanate, at least one isocyanate-reactive polymer and at least one, optionally substituted, phenol selected from the group consisting of 1,4-dihydroxybenzene, 1,3-dihydroxybenzene, 1,2-dihydroxybenzene, 1,3-dihydroxytoluene, 3,5-dihydroxybenzoates, bis(4-hydroxyphenyl)methane (bisphenol F), bis(4-hydroxyphenyl) sulfone (bisphenol S), naphthoresorcinol, dihydroxynaphthalene, dihydroxy-anthraquinone, dihydroxybiphenyl, 3,3-bis(p-hydroxyphenyl)phthalides, 5,5-bis(4-hydroxyphenyl)hexahydro-4,7-methanoindane, phenolphthalein, fluorescein, 4,4'-[bis(hydroxyphenyl)-1,3-phenylenebis(1-methylethylidene)] (bisphenol M), 4,4'-[bis-(hydroxyphenyl)-1,4-phenylenebis(1-methylethylidene)] (bisphenol P), o,o-diallylbisphenol A, dicresols prepared by reacting cresols with diisopropylidenebenzene, phloroglucinol, gallic ester, cresol novolacs having an —OH functionality of from 2.0 to 3.5, and isomers thereof,
at least one thixotropic agent C based on a urea derivative in a nondiffusing carrier material; and
at least one curing agent D for epoxy resins, which is activated by elevated temperature.

2. The composition as claimed in claim 1, wherein the epoxide adduct A is obtainable from the reaction
of at least one dicarboxylic acid and at least one diglycidyl ether;
or
of at least one bis(aminophenyl) sulfone isomer or of at least one aromatic alcohol and at least one diglycidyl ether.

3. The composition as claimed in claim 2, wherein the dicarboxylic acid is at least one dimeric $C_4$-$C_{20}$ fatty acid, and the diglycidyl ether is bisphenol A diglycidyl ether, bisphenol F diglycidyl ether or bisphenol diglycidyl ether.

4. The composition as claimed in claim 2, wherein the aromatic alcohol is selected from the group consisting of 2,2-bis(4-hydroxyphenyl)propane, bis(4-hydroxyphenyl)methane, bis(4-hydroxyphenyl) sulfone (=bisphenol S), hydroquinone, resorcinol, pyrocatechol, naphthohydroquinone, naphthoresorcinol, dihydroxynaphthalene, dihydroxyanthraquinone, dihydroxybiphenyl, 3,3-bis(p-hydroxyphenyl) phthalides, 5,5-bis(4-hydroxyphenyl)hexahydro-4,7-methanoindane, 4,4'-[bis(hydroxyphenyl)-1,3-phenylenebis(1-methylethylidene)] (=bisphenol M), 4,4'-[bis(hydroxyphenyl)-1,4-phenylenebis(1-methyl-ethylidene)] (=bisphenol P) and all isomers of the above mentioned compounds, and the diglycidyl ether is bisphenol A diglycidyl ether, bisphenol F diglycidyl ether or bisphenol A/F diglycidyl ether.

5. The composition as claimed in claim 1, wherein the polymer B is soluble or dispersible in epoxy resins.

6. The composition as claimed in claim 1, wherein the isocyanate-reactive polymer is a polyol selected from the group consisting of the polyoxyalkylenepolyols, polyhydroxy-terminated polybutadienepolyols, styrene/acrylonitrile-grafted polyetherpolyols, polyhydroxy-terminated acrylonitrile/butadiene copolymers, polyesterpolyols and polycarbonatepolyols.

7. The composition as claimed in claim 1, wherein the isocyanate-reactive polymer is an $\alpha,\omega$-polyalkylene glycol having $C_2$-$C_6$-alkylene groups or having mixed $C_2$-$C_6$-alkylene groups.

8. The composition as claimed in claim 1, wherein the isocyanate-reactive polymer has an equivalent weight of 600-6000 g/equivalent of NCO-reactive groups.

9. The composition as claimed in claim 1, wherein the polyisocyanate is a diisocyanate selected from the group consisting of hexamethylene diisocyanate (HDI), isophorone diisocyanate (IPDI), trimethylhexamethylene diisocyanate (TMDI), methylenediphenyl diisocyanate (MDI) and toluene diisocyanate (TDI).

10. The composition as claimed in claim 1, wherein the proportion by weight of all polymers B of the formula (I) is from 5 to 40% by weight based on the weight of the total composition.

11. The composition as claimed in claim 1, wherein the carrier material of the thixotropic agent C is a blocked polyurethane prepolymer.

12. The composition as claimed in claim 1, wherein the urea derivative in the thixotropic agent C is a product of the reaction of an aromatic monomeric diisocyanate with an aliphatic amine compound.

13. The composition as claimed in claim 1, wherein the total proportion of the thixotropic agent C is 5-40% by weight based on the weight of the total composition.

14. The composition as claimed in claim 1, wherein the proportion of the urea derivative is 5-50% by weight based on the weight of the thixotropic agent C.

15. The composition as claimed in claim 1, wherein the curing agent D is a latent curing agent selected from the group consisting of dicyandiamide, guanamines, guanidines and aminoguanidines.

16. The composition as claimed in claim 1, wherein the total proportion of the curing agent D is 1-10% by weight based on the weight of the total composition.

17. The composition as claimed in claim 1, wherein at least one filler E is additionally present.

18. The composition as claimed in claim 17, wherein the total proportion of the filler E is 5-30% by weight based on the weight of the total composition.

19. The composition as claimed in claim 1, wherein at least one reactive diluent F carrying epoxide groups is additionally present.

20. The composition as claimed in claim 1, wherein the composition, after curing, has a low-temperature fracture energy, measured according to DIN 11343, of more than 10 J at −20° C. and of more than 7 J at −40° C.

21. An impact strength modifier terminated with epoxide groups and of the formula (I):

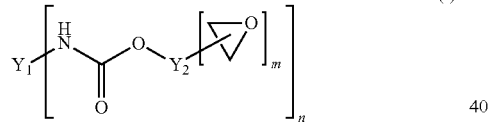

(I)

in which:
- $Y_1$ is an n-valent moiety derived from a linear or branched polyurethane prepolymer terminated with isocyanate groups by removal of the terminal isocyanate groups from the polyurethane prepolymer;
- $Y_2$ is a moiety of an aliphatic, cycloaliphatic, aromatic or araliphatic epoxide containing a primary or secondary hydroxyl group after removal of the hydroxide and epoxide groups;
- n is 2, 3 or 4;
- m is 1, 2 or 3;
- and the impact strength modifier has at least one aromatic structural element, which is bound in the polyurethane prepolymer via urethane groups, wherein the $Y_1$ moiety of the impact strength modifier simultaneously has structural elements of the formulae (IV) and (V)

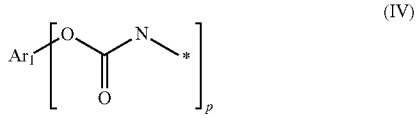

(IV)

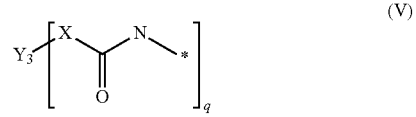

(V)

in which:
- p is 2, 3 or 4;
- q is 2, 3 or 4;
- X is S, O or NH;
- $Ar_1$ is a p-valent, optionally substituted, aromatic moiety, wherein the aromatic moiety is directly bound to the urethane groups;
- $Y_3$ is a q-valent, optionally chain-extended, moiety of an isocyanate-reactive polymer after removal of the terminal amino, thiol or hydroxyl groups; and
- * is the linkage point to the remainder of the polyurethane prepolymer wherein the impact strength modifier is obtained from the reaction of a monohydroxyepoxide of the formula (II) and of a linear or branched polyurethane prepolymer terminated with isocyanate groups of the formula (III)

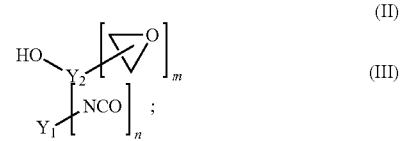

(II)

(III)

wherein the polyurethane prepolymer of the formula (III) is obtained from the reaction of at least one polyisocyanate, at least one isocyanate-reactive polymer and at least one, optionally substituted, phenol selected from the group consisting of 1,4-dihydroxybenzene, 1,3-dihydroxybenzene, 1,2-dihydroxybenzene, 1,3-dihydroxytoluene, 3,5-dihydroxybenzoates, bis(4-hydroxyphenyl)methane (bisphenol F), bis(4-hydroxyphenyl) sulfone (bisphenol S), naphthoresorcinol, dihydroxynaphthalene, dihydroxy-anthraquinone, dihydroxybiphenyl, 3,3-bis(p-hydroxyphenyl)phthalides, 5,5-bis(4-hydroxyphenyl)hexahydro-4,7-methanoindane, phenolphthalein, fluorescein, 4,4'-[bis(hydroxyphenyl)-1,3-phenylenebis(1-methylethylidene)] (bisphenol M), 4,4'-[bis-(hydroxyphenyl)-1,4-phenylenebis(1-methylethylidene)] (bisphenol P), o,o-diallylbisphenol A, dicresols prepared by reacting cresols with diisopropylidenebenzene, phloroglucinol, gallic ester, cresol novolacs having an —OH functionality of from 2.0 to 3.5, and isomers thereof.

22. A one-component adhesive comprising the composition of claim 1.

23. A two-component adhesive comprising the composition of claim 21, wherein this impact strength modifier is a constituent of the first component and at least one polyamine or at least one polymercaptan is a constituent of the second component.

24. A composition comprising heat-stable materials bonded together with the one-component adhesive of claim 22.

25. An automotive body-shell construction adhesive comprising the one-component adhesive of claim 22.

26. A method for the adhesive bonding of heat-stable materials, wherein these materials are brought into contact with a composition as claimed in claim 1 and comprises a subsequent step of curing at a temperature of 100-220° C.

* * * * *